US012635982B2

(12) United States Patent
Meyer et al.

(10) Patent No.: US 12,635,982 B2
(45) Date of Patent: May 26, 2026

(54) SYSTEM AND METHOD FOR TESTING INTRAVASCULAR ULTRASOUND CATHETERS

(71) Applicants: Chris Meyer, Windermere, FL (US);
Seth Masek, Dover, FL (US)

(72) Inventors: Chris Meyer, Windermere, FL (US);
Seth Masek, Dover, FL (US)

( * ) Notice: Subject to any disclaimer, the term of this patent is extended or adjusted under 35 U.S.C. 154(b) by 75 days.

(21) Appl. No.: 18/941,530

(22) Filed: Nov. 8, 2024

(65) Prior Publication Data

US 2026/0130648 A1 May 14, 2026

(51) Int. Cl.
*A61B 8/00* (2006.01)

(52) U.S. Cl.
CPC .......... *A61B 8/4494* (2013.01); *A61B 8/4461* (2013.01)

(58) Field of Classification Search
CPC ...... A61B 8/4494; A61B 8/4461; A61B 8/587
See application file for complete search history.

(56) References Cited

U.S. PATENT DOCUMENTS

| | | | | |
|---|---|---|---|---|
| 5,485,845 A | * | 1/1996 | Verdonk | G01S 15/874 |
| | | | | 600/463 |
| 5,699,806 A | * | 12/1997 | Webb | G01S 15/894 |
| | | | | 600/445 |
| 2008/0177139 A1 | * | 7/2008 | Courtney | A61B 5/742 |
| | | | | 600/109 |
| 2016/0157828 A1 | * | 6/2016 | Sumi | G01N 29/46 |
| | | | | 702/189 |

* cited by examiner

*Primary Examiner* — Joel Lamprecht
(74) *Attorney, Agent, or Firm* — Robert Brownstein

(57) ABSTRACT

The invention is a system for testing IVUS catheters and a method for using the test system.

7 Claims, 11 Drawing Sheets

100

101

103

102

100

101

103

102

401

102

500

100

501

502

600

602

601

603

701

702

801

802

803

803

901

1101     1102     1103     1104

SYSTEM AND METHOD FOR TESTING INTRAVASCULAR ULTRASOUND CATHETERS

TECHNICAL FIELD

The invention is a system and method for testing the transducers in a solid-state intravascular ultrasound catheter.

BACKGROUND OF INVENTION

Cardiovascular disease is responsible for approximately 20-25 percent of all deaths in the United States, making it the leading cause of mortality in the country.

Intravascular ultrasound (IVUS) is an adjunct to traditional ultrasound and angiography to evaluate cardiovascular disease and to assist in treatment.

An IVUS catheter is a medical device used to visualize the inside of blood vessels. It is a catheter with an ultrasound transducer at the distal tip that is inserted into the vessel and using ultrasound beams striking and reflecting off of the blood vessel wall, it can it provides detailed images of the morphology of the vessel walls and surrounding structures. IVUS is helpful in evaluating the severity and extent of plaque buildup in arteries. It is used in angioplasty and stent placement to ensure optimal position and expansion of devices within the vessel. After stenting, IVUS can assess the stent's deployment and identify complications, such as in-stent restenosis. IVUS can differentiate between different types of plaque morphology which is useful in determining treatment strategies.

There are two fundamental types of IVUS catheters, one that has a single ultrasound transducer that is rapidly rotated by electro-mechanical means; and one in which many transducers are arranged like a collar within the catheter shaft such that the transducers create a circular field of incident and reflected ultrasound waves essentially aligned transversely to the vessel axis. This second type is known as a solid-state IVUS catheter. Both transducer types are common in modern IVUS catheters.

An original-equipment-manufacturer's (OEM's) IVUS catheter will have been rigorously tested before first use. After use, though, one or more transducers may be degraded. Thus, a reprocessed IVUS catheter that meets all FDA requirements for safe use after rigorous cleaning and sterilization may not perform as accurately as a first-use IVUS catheter if there has been significant transducer degradation.

The availability of reprocessed IVUS catheters can lower the cost of the overall procedure significantly. But, a degraded-performance device may not provide an accurate intravascular image. Therefore, a reprocessed IVUS catheter, as well as a first-use catheter, must be tested to determine that some minimum number of transducers are operating properly to ensure quality imaging results. Visual inspection usually cannot determine a problem transducer. Thus, there is need for an IVUS catheter testing system and method that is accurate and efficient.

BRIEF DESCRIPTION OF INVENTION

The invention is a test system and method of use that can accurately and efficiently test all the transducers in a reprocessed or first-use IVUS catheter to determine if the catheter will provide acceptable performance.

An image produced through use of an IVUS catheter is only as accurate as the operation of the combination of ultrasound transducers each contains. The role of each transducer is to, when electrically excited, emit an ultrasound wave beam that reflects off the blood-vessel wall surface and a portion of which is then received by the transducer to produce an analog electrical signal analogous to the magnitude of that reflected wave.

Ideally, all the transducers should have essentially identical characteristics regarding the magnitude of the transmitted ultrasound wave when excited electrically, and the analogous electrical conversion of the reflected ultrasound wave when received. If an identical electrical signal is used to excite each transducer to produce a resulting ultrasound wave, that wave should have essentially the same characteristics for each transducer. Conversely, each transducer that receives an identical ultrasound wave should produce an essentially identical analog signal.

In reality, there will be some variation within any sample of identically manufactured transducers. These differences should not affect a predetermined measure of acceptable performance. However, if some number of transducers is shown to fall outside a range of predetermined test results, the overall quality of the images produced by the IVUS catheter may fall below acceptable performance. In addition, if the troublesome transducers tend to be clustered, a smaller number of such transducers may render the overall IVUS catheter performance as unacceptable.

The tester herein disclosed is a system and method of use that works in conjunction with the IVUS catheter system, provides a test fixture wherein each transmitted wave experiences essentially the same reflection coefficient resulting in essentially identical reflected waves then received by each transducer. Therefore, significant differences in a transducer's analog electrical signal from those of other transducers can be seen as subpar test performance.

By testing each transducer using an acoustic test fixture that is operative to produce essentially identical reflection coefficients, and measuring the analog electrical signal produced by each transducer, one can pinpoint and locate every transducer whose test result is below some predetermined level of acceptable performance and, therefore, using predetermined acceptance criteria, determine if an IVUS catheter, as a whole, is acceptable for use or not.

The system makes use of three subsystems—an acoustic test fixture, a test-control subsystem, and a computing subsystem. By monitoring signals conveyed between an IVUS catheter and IVUS-catheter control subsystem, one can use monitored timing signals to selectively capture each transducer's reflected wave analog signal, digitize that signal, associate it with the transducer that produced it, and get a set of values representing each transducer. It can be repeated for some predetermined number of samples, then the value per transducer are averaged and compared to a range of known-good values. By knowing how many transducers fall below an acceptable range, and where they are located in relation to one another, a very reliable and repeatable test can be done to determine if a first-use or reprocessed IVUS catheter demonstrates acceptable performance.

DETAILED DESCRIPTION OF INVENTION

An IVUS catheter is a critical device for finding and treating vascular damage and obstructions. It enables medical personnel to see inside a blood vessel to determine the health of vessel walls and degree of obstruction of blood flow through a vessel's lumen.

Currently, the solid-state IVUS catheter with a multitude of ultrasound transducers is the device of choice for intravascular examination.

Figure 1:
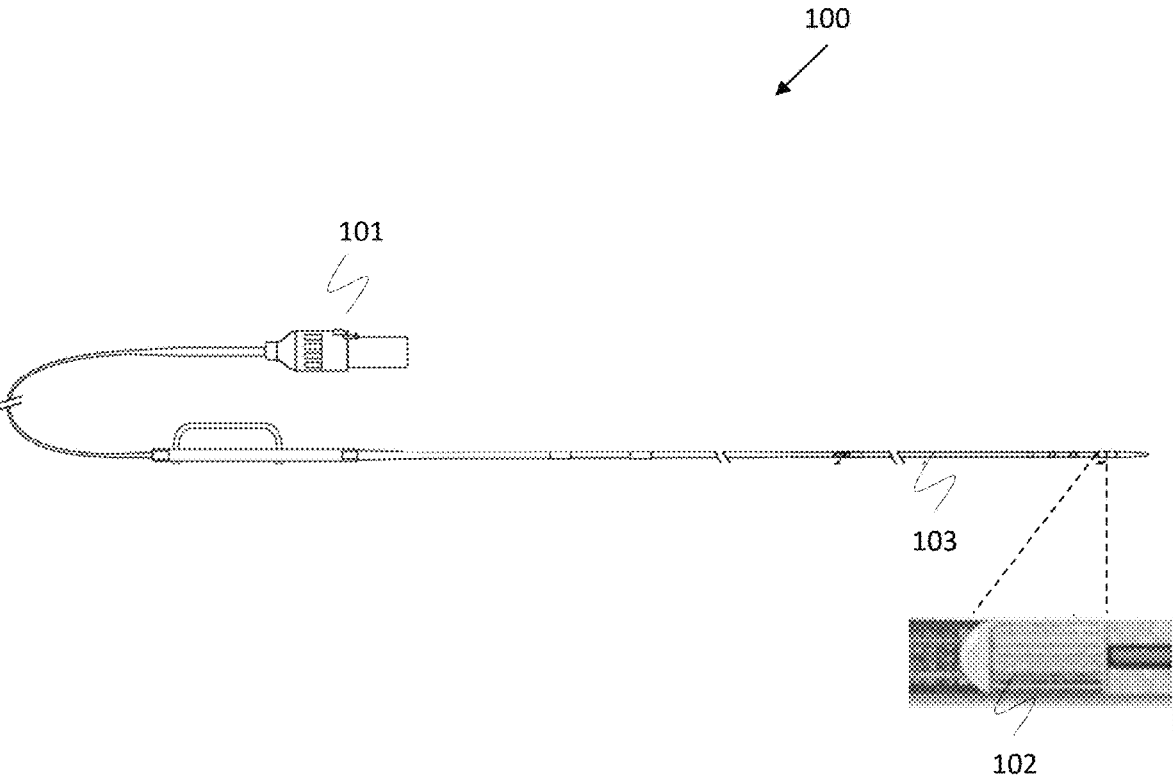
FIG. 1 illustrates a solid-state IVUS catheter and its transducer portion.

An OEM IVUS system comprises the IVUS catheter subsystem, a PIM subsystem and a control subsystem. As shown in FIG. 1, the IVUS catheter (100) comprises a connector (101) that can be connected to a PIM, a shaft (103) that is inserted intravascularly, and a collar made up of a multitude of individual transducers (102) inside the shaft at the distal end of the catheter.

Figure 2:
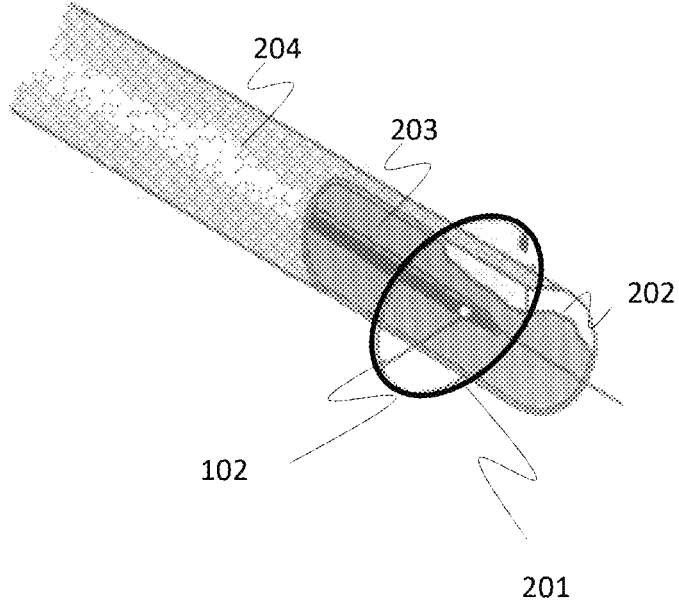
FIG. 2 illustrates the device in FIG. 1 wherein it is inserted into a blood vessel showing its orientation in relation to the vessel's wall.

When an IVUS catheter is inserted in a blood vessel, its shaft is oriented axially and as shown in FIG. 2, the transducers transmit and receive ultrasound wave beams essentially transverse to the blood-vessel axis. The transducers transmit and receive the ultrasound wave beams to provide a circular pattern of incident-wave targets (201). The wave beams are incident to the vessel wall and any materials that may adhere to the vessel wall (202). The lumen, the hollow inside the vessel through which blood flows (203), and obstructions (202), are exposed by the incident and reflected waves emitted and received by the multiple transducers.

Figure 3:
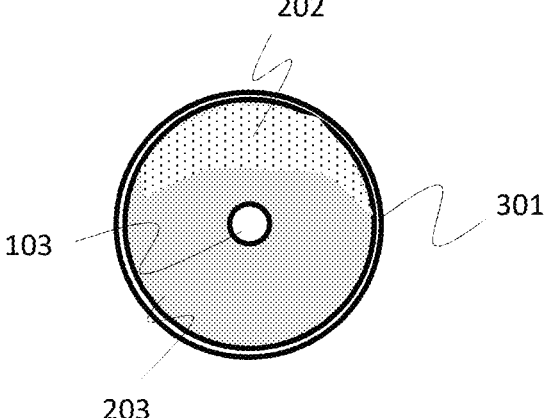
FIG. 3 illustrates a cut-away view of a blood vessel showing the IVUS catheter oriented axially and showing the lumen and some obstructive material adhering to the vessel wall. It also shows the image produced by the IVUS catheter system showing the lumen and obstructive material.
Figure 3:
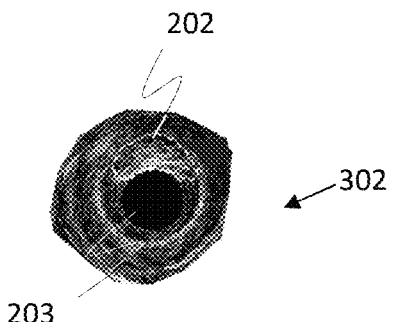

In FIG. 3, a cut-away view of a blood vessel, the IVUS catherter's shaft (103) is at or near the middle of the vessel and the emitted and received wave beams travel through the lumen 203 and reflect off the unobstructed wall surface (301) and material obstructions (202). The IVUS control subsystem uses the reflected wave beams passing through the lumen, back to the transducers, to construct a visual representation of the circular slice of blood vessel (302). As the catheter is moved axially, the visual slices provide a three-dimensional view of the intravascular conditions.

Figure 4:
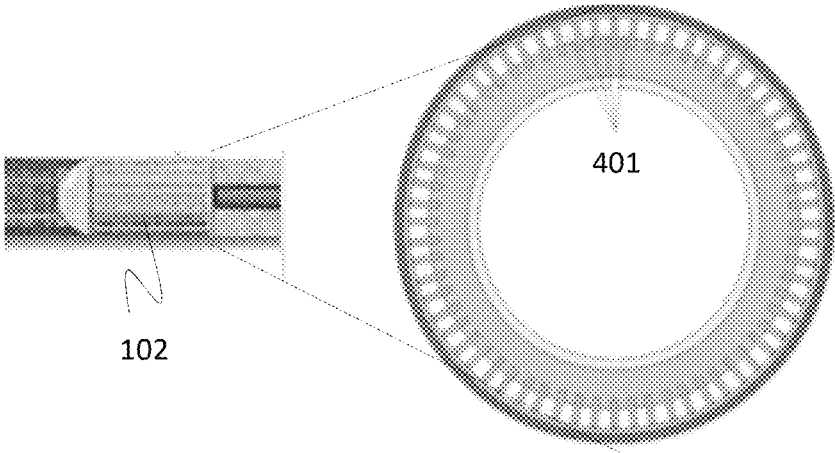
FIG. 4 shows a cut-away view of the IVUS catheter, along its axis, showing the many transducers in position.

The accuracy of the view is in large part dependent upon the quality and consistency of each of the multitude of transducers. As shown in FIG. 4, the transducer collar (102)

and a cut-away view of the IVUS catheter's shaft shows the peripheral positions of a multitude of ultrasound transducers (401).

Ultimately, to accurately test the IVUS catheter each of the transducers must be tested.

Figure 5:
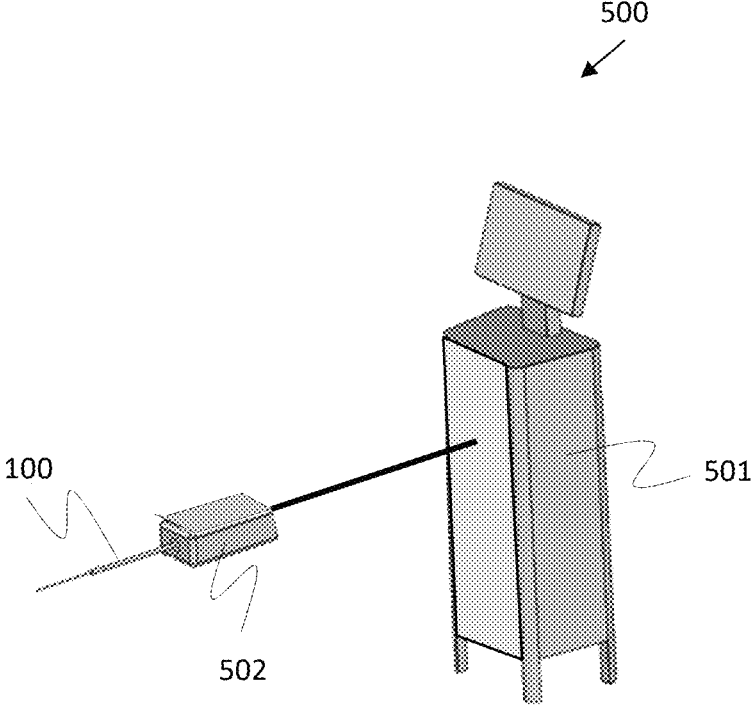
FIG. 5 shows an example of an OEM IVUS system with its controller subsystem, patient-interface module (PIM) and IVUS catheter.

In FIG. 5, the OEM IVUS system (500) comprises an IVUS catheter control subsystem (501), the IVUS catheter (100) and an intermediary subsystem called a patient=interface module (PIM) shown as 502. Typically, the control subsystem and PIM are preserved for use in multiple intravascular operations but the catheter is considered a single-use subsystem. That is, it may be detached after a first use, and discarded; or it may be reprocessed for a subsequent use. Under FDA rules, a reprocessed IVUS catheter must meet stringent criteria for structural integrity, cleanliness and sterilization.

However, the FDA rules do not stipulate functional criteria, and it is possible that an otherwise, FDA-compliant, reprocessed IVUS catheter subsystem may not provide sufficiently accurate and resolute reflected-wave analog signals. Thus, to ensure that a reprocessed or first-use IVUS transducer meets a predetermined standard of overall catheter performance, each ultrasound transducer must be tested.

To provide an accurate and efficient test system and method, this invention makes use of the OEM IVUS system and adds additional testing subsystems to the mix.

Figure 6:
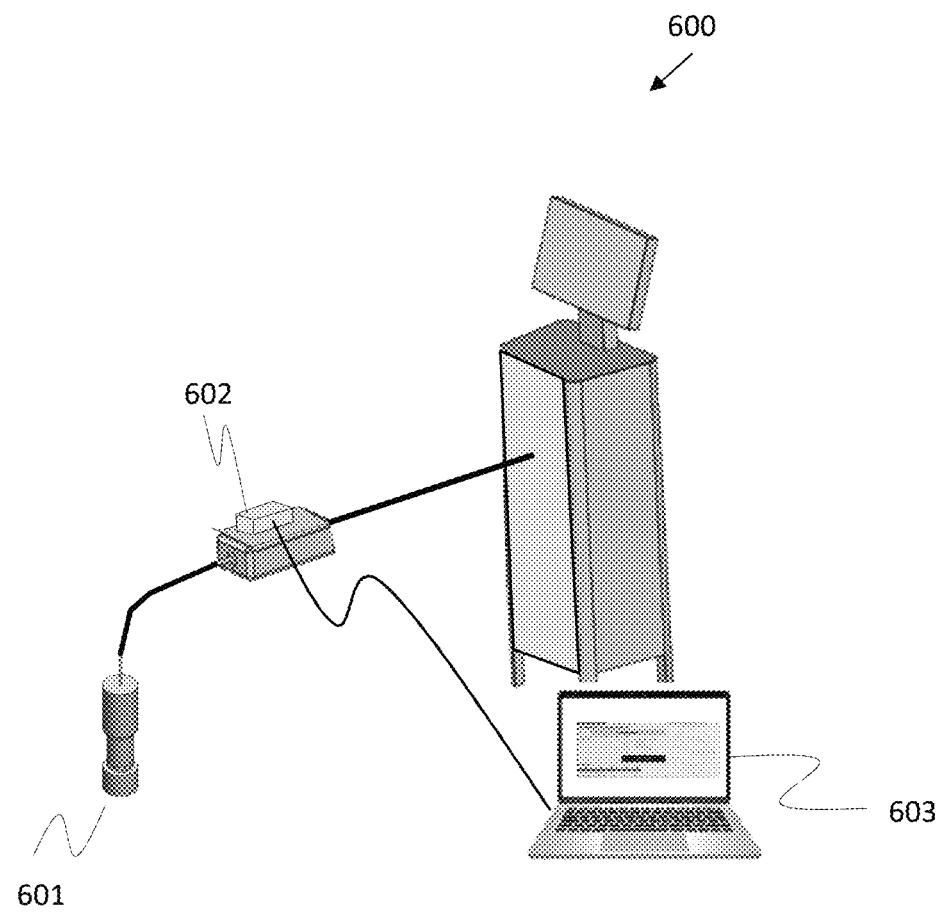
FIG. 6 show the invention test system subsystems augmenting the OEM system from FIG. 5.

As shown in FIG. 6, the three added subsystems, which define this test system, are an acoustic test fixture (601), a test-control subsystem (602), and a computing subsystem (603).

Figure 7:
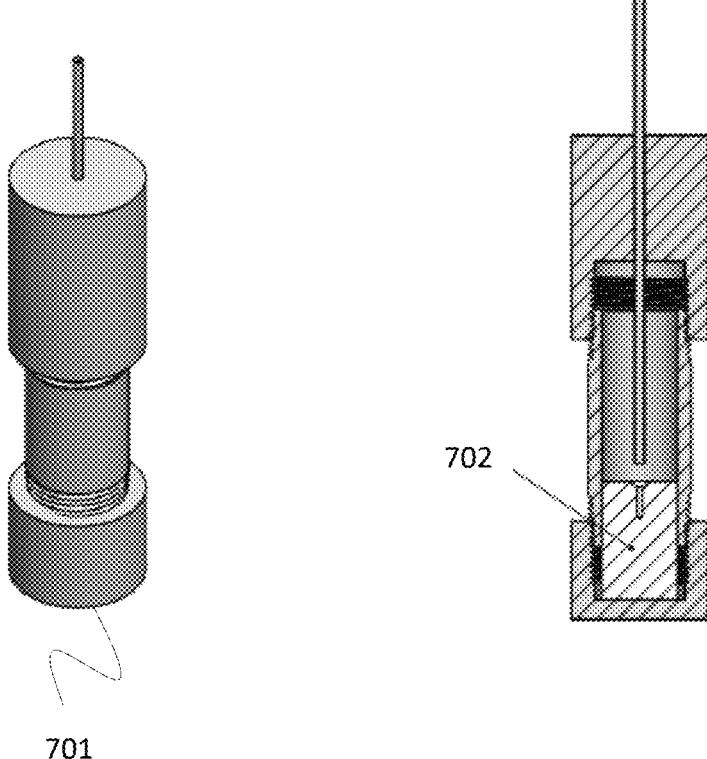
FIG. 7 illustrates an embodiment of the acoustic test fixture.

The acoustic test fixture (FIGS. 7, 701 and 702) is meant to provide a known standard for acoustic-wave reflection coefficient such that when an IVUS catheter to be tested is inserted and fixed in position inside this subsystem (702), its incident waves reflected off the tubular acoustic test fixture will have essentially the same reflection experience. Assuming each transducers incident wave has essentially the same wave energy, the reflected wave portion received by the transducer that emitted the incident wave, should receive a reflected wave with essentially the same wave energy. Assuming that is the case, then when each transducer converts the acoustic wave energy into an equivalent electrical signal, those signals should all be essentially equal. By sampling just the electrical signal provided by each transducer, allowing for transducer manufacturing variables, there will be a range of values that are still consistent with acceptable operation. However, a measurement that falls below that range of values may be indicative of an incident wave having too low wave energy, or a transducer producing a too low equivalent electrical signal, or both. In any case, it indicates that a transducer fails to meet a predetermined standard. Through repeated testing of random IVUS catheter samples, one can find a range of analog electrical signal values consistent with appropriate accuracy. As such, the acoustic test fixture is a first step in establishing testing uniformity.

Figure 11:
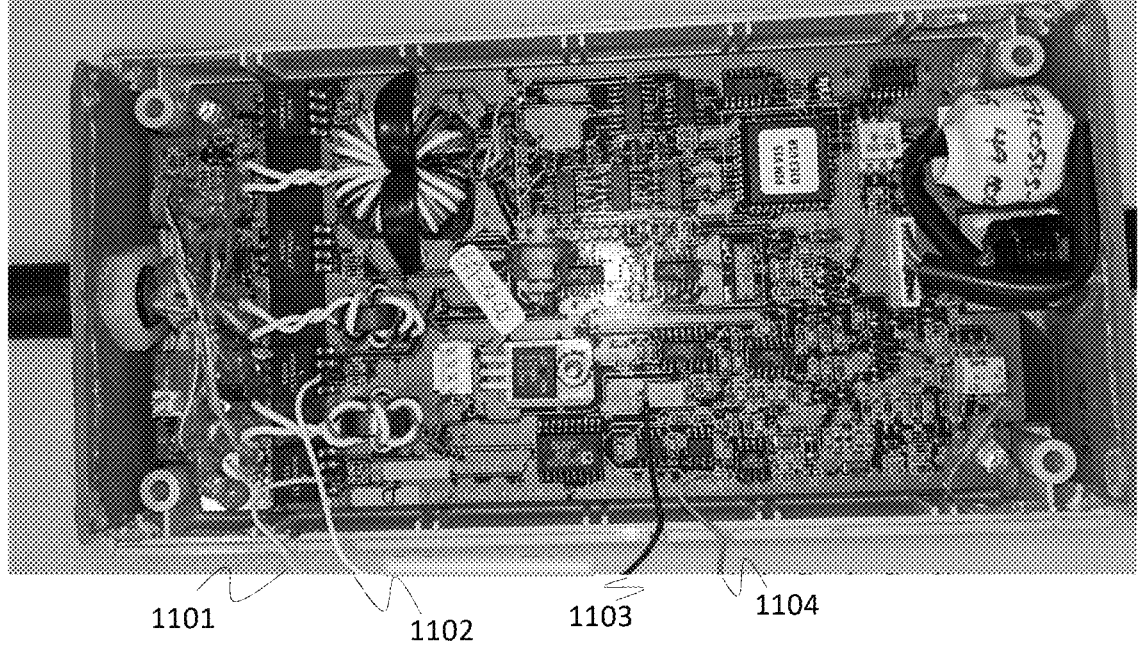
FIG. 11 shows how an OEM PIM can be tapped so as to monitor Tx, Rx, signal ground and a reflected waves analog signal.

The test-control subsystem (602) monitors control and reflected-wave analog signals as they pass between the OEM control subsystem and IVUS catheter subsystem. FIG. 11 shows how one embodiment of the invention makes use of a PIM to tap and monitor receive (Rx)-trigger signals (1101), transmit (Tx)-trigger signals (1102), signal ground return (1103) and reflected-wave analog signals (1104). The goal, here, is to use the control signals to control the capture of clean, reflected-wave analog signals and associate each with a transducer that is associated with it. Ultimately, every transducer's reflected-wave analog signal will be rectified and digitized inside the test-control subsystem under control of a microcontroller and its embedded-control program.

The third subsystem—the computing subsystem (603)—is shown as a laptop computer in FIG. 6. Running an IVUS testing program the computing subsystem will receive data from the test-control subsystem enabling it to store each digitized value and associate it with each transducer. Again, on the basis of experimental results, the number of samples for each transducer that will provide a valid measure of its performance can be found and used as a predetermined transducer pass/fail limit, and the number of failed transducers and their positions relative to each other can be used to predetermine pass/fail qualifications for the IVUS catheter as a whole.

The following Figures and descriptions are exemplary of an embodiment of the IVUS catheter testing system.

Figure 8:
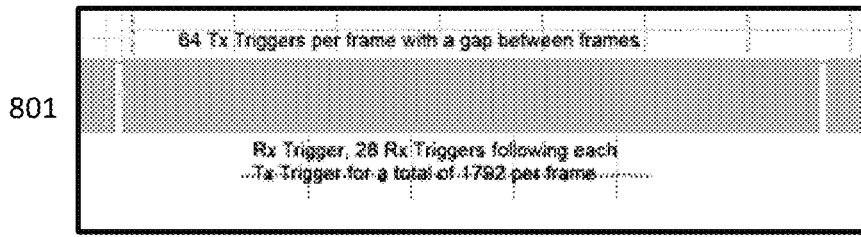
FIG. 8 shows the Tx and Rx trigger signals conveyed from and to the controller subsystem and to and from the IVUS catheter.
Figure 8:
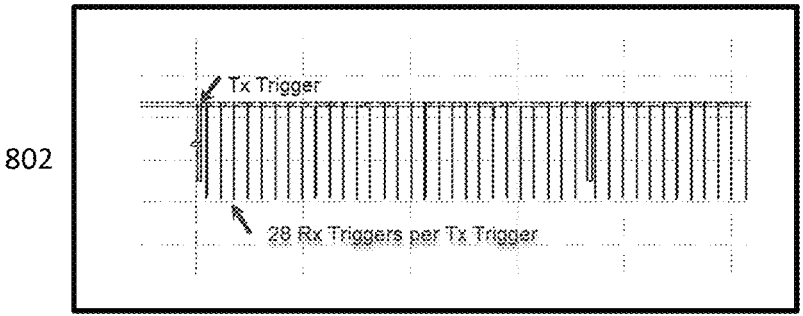
Figure 8:
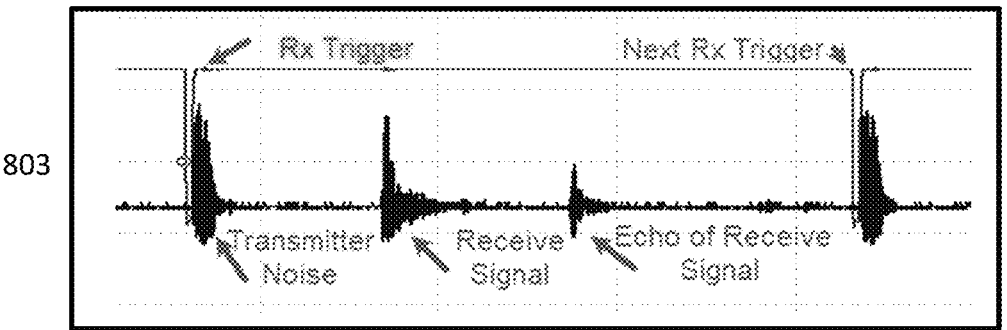

The OEM IVUS system and the embodiment of the IVUS catheter test system are based on that OEM's operational signals. As shown in FIG. 8, 801, 64 Tx triggers occur per frame followed by a time gap. In addition, 28 Rx triggers follow each Tx trigger (802) making for a total of 1,792 Tx and Rx triggers per frame. Using the time gap, the test-control subsystem can determine the start of each new frame. As shown in 803, each Rx trigger will invoke a signal train comprising transmitter noise, the desired receive signal, and a receive-signal echo.

Figure 9:
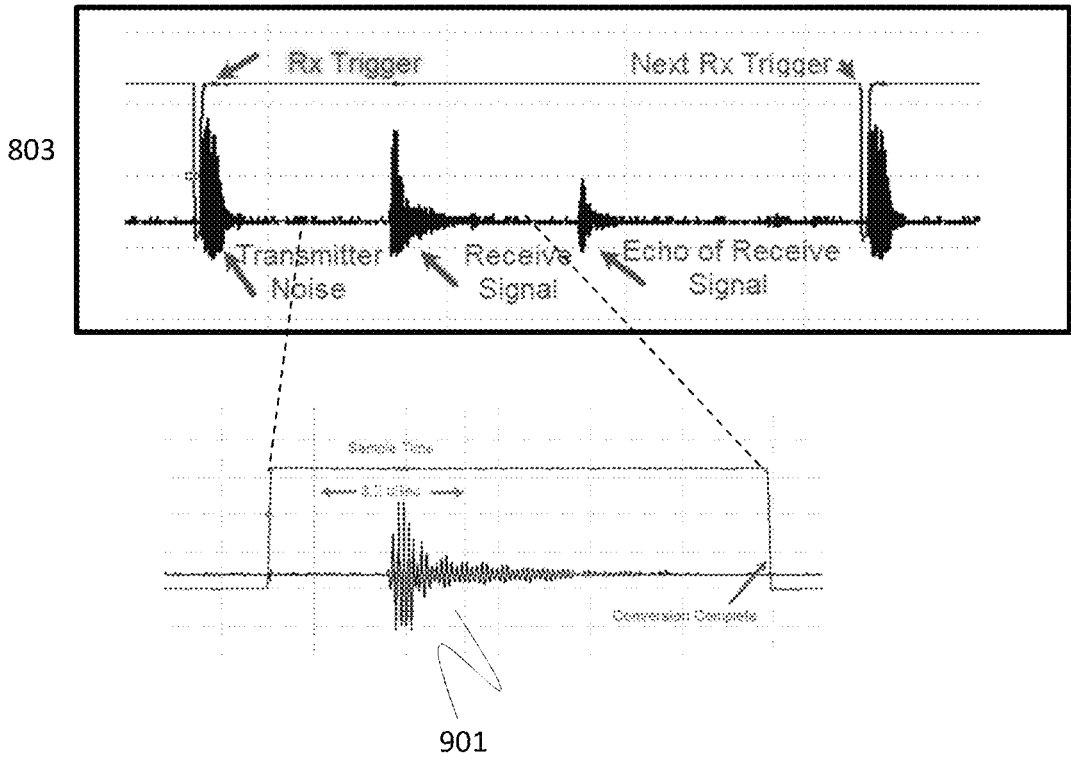
FIG. 9 illustrates how in one embodiment the Tx and Rx triggers are used to establish a sample period for capturing a reflected wave's analog signal.

The embedded-control program in the test-control subsystem establishes a sample time by controlling internal switching such that only the desired receive signal is passed through while transmitter noise and echo are not passed through (FIG. 9, 901).

Figure 10:
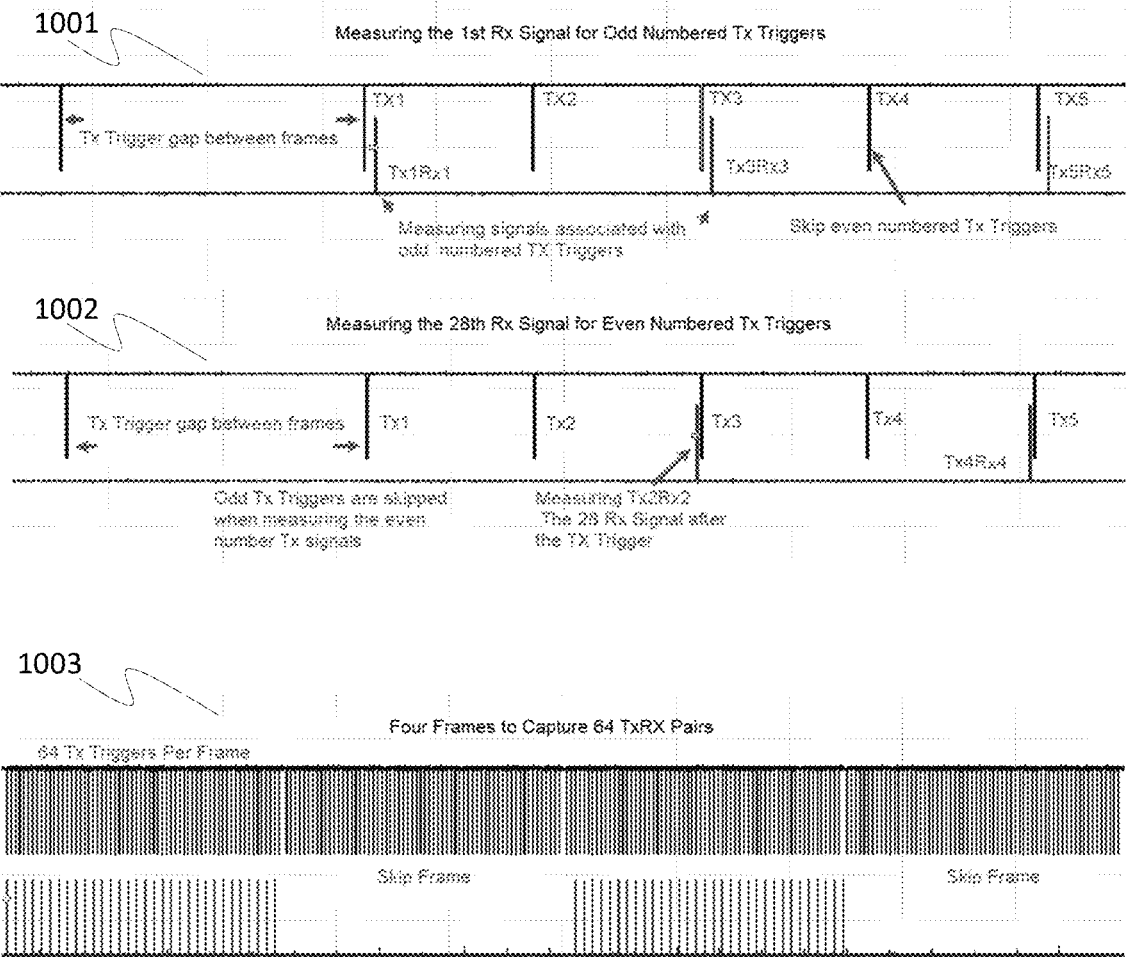
FIG. 10 illustrates how in one embodiment the Tx and Rx triggers are used to sample every other frame to allow for test-system settlement and noise avoidance.

In FIG. 10, in this embodiment, following the inter-frame gap, a first trigger signal (Tx1) evokes an Rx trigger (Tx1Rx1) followed by Rx triggers with subsequent odd-numbered Tx triggers (1001). Regarding even-numbered Tx triggers, an Rx trigger is invoked to measure the 28th Rx triggered value (1002). As shown in 1003, intervening frames are skipped so it takes four frame times (rather than two) to capture the readings of all 64 ultrasound transducers. By repeating this process for some predetermined number of samples, the readings can be averaged smoothing out artifact and extraneous readings and arriving at an averaged reading that can then be compared to a range of readings for known-good transducer performance.

The FIGS. 7 through 11 are based on one embodiment of this invention system and its method of use. Where an IVUS catheter may have a different number of ultrasound transducers, or a different control-signal regime, the embedded-control algorithms for slaved timing and switching may require modifications.

The acoustic test fixture as shown is exemplary. It may be made of metals but could be made of non-metals, also.

The test-control subsystem can be implemented using highly-integrated electronic components, or less-integrated discrete components. It is shown in close proximity to the OEM PIM so as to keep the conductive interconnections short to reduce ohmic losses and timing latencies.

It should be noted that this embodiment makes use of OEM IVUS controller and PIM subsystems. However, a test control subsystem could comprise an internal IVUS controller subsystem that provides Rx and Tx signals to the OEM catheter subsystem which simulates those conveyed by the OEM IVUS controller with PIM subsystems. In that case, the test controller subsystem could be connected directly to the OEM catheter subsystem and provide timing- and switching-based operation based on its internal IVUS controller subsystem. This would allow an alternative for capturing the reflected wave's analog signal that does not use the OEM IVUS controller and PIM subsystems. The same qualifications would be applied to the reflected wave's analog signal as before, and an OEM catheter's transducers could be tested in essentially identical fashion. Therefore the term "IVUS controller subsystem" is defined as an OEM or internal IVUS control subsystem, and the term "IVUS PIM" is defined as either an external PIM as described in the embodiment using the OEM subsystems, or an internal interface as used in an internal IVUS controller embodiment.

The exemplary drawings and descriptions should not be read as limiting the scope of claims.

What is claimed is:

1. A system for testing IVUS catheters comprising:
an IVUS catheter-control subsystem operative to control operation of an IVUS catheter;
an IVUS catheter comprising a plurality of ultrasound transducers;
the plurality of ultrasound transducers operative to produce ultrasound acoustic waves when stimulated electrically, and to produce analog electrical signals when stimulated acoustically;
an IVUS PIM operative to convey signals between the IVUS catheter-control subsystem and the IVUS catheter;
an acoustic test fixture operative to reflect ultrasound acoustic waves when struck by incident acoustic waves;
the acoustic test fixture comprising metallic tubing; and
the IVUS catheter, when inserted into the acoustic test fixture and fixed in place, configured to emit acoustic waves perpendicular to the metallic tubing's axis,
a test-control subsystem operative to:
monitor control signals conveyed between the IVUS catheter-control system and the IVUS catheter;
correlate the monitored signals with each of the plurality of ultrasound transducers;
capture the analog electrical signals, when stimulated acoustically, from each of plurality of ultrasound transducers;
perform analog-to-digital conversion on each of the analog electrical signals captured from the plurality of ultrasound transducer analog signals resulting from acoustic stimulation; and
output the digitized metrics for each of the plurality of ultrasound analog electrical signals;
a computing subsystem operative to:
receive the digitized metrics for each of the plurality of ultrasound analog electrical signals;
average the digitized metrics received from each of the plurality of ultrasound transducers;
compare the averaged digitized metrics for each of the plurality of ultrasound transducers to known-good values; and
determine for each of the ultrasound transducers whether or not the averaged metrics fall within a range of values indicative of predetermined acceptable operation.

2. A system as in claim 1 wherein:
the test-control subsystem comprises:
timing circuitry slaved to monitored control signals conveyed between the IVUS catheter-control subsystem and the IVUS catheter.

3. A system as in claim 1 wherein:
the test-control subsystem comprises:

switching circuitry slaved to the timing circuitry operative to capture predetermined portions of the analog electrical signals captured from each of the plurality of ultrasound transducers.

4. A system as in claim 1 wherein:
the test-control subsystem comprises:
 an analog-to-digital converter operative to convert the analog electrical signals into digital equivalents.

5. A system as in claim 1 wherein:
the test-control subsystem comprises:
 a microcontroller; and
 an embedded-control test program.

6. A system as in claim 1 wherein:
the computing subsystem comprises:
 a central processing unit subsystem;
 a mass-storage subsystem;
 a program-memory subsystem;
 a dynamic random-access-memory subsystem;
 an input-output subsystem;
 a keyboard data-entry subsystem; and
 a display subsystem.

7. A system as in claim 1 wherein:
the computing subsystem comprises:
 at least one program operative to:
  control receiving digitized analog electrical signal data from the test-control subsystem;

organize the digitized analog electrical signal data correlated with each of the plurality of ultrasound transducers;

determine that the digitized analog electrical signal data from each of the plurality of ultrasound transducers has been received, organized and stored;

repeat capturing the digitized analog electrical signal data from each of the plurality of ultrasound transducers for a predetermined number samples;

average the digitized analog electrical signal data from each of the plurality of ultrasound transducers upon completion of the predetermined number of samples;

compare the averaged data for each of the plurality of ultrasound transducers to a predetermined range of values indicative of acceptable operation;

report test results for each of the plurality of ultrasound transducers indicating, in each case, whether each result is acceptable or unacceptable;

determine based on the report test results whether the IVUS catheter, as a whole, passes or fails predetermined pass or fail criteria.

\* \* \* \* \*